United States Patent [19]
Panin et al.

[11] Patent Number: 5,508,801
[45] Date of Patent: Apr. 16, 1996

[54] METHOD AND APPARATUS FOR NONDESTRUCTIVE TESTING OF THE MECHANICAL BEHAVIOR OF OBJECTS UNDER LOADING UTILIZING WAVE THEORY OF PLASTIC DEFORMATION

[75] Inventors: Victor Y. Panin; Lev B. Zuev; Pavel V. Makarov; Valery E. Yegorushkin; Vadim V. Gorbatenko; Vladimir I. Danilov, all of Tomsk, Russian Federation

[73] Assignees: Kabushikigaisya Hutech, Tokyo, Japan; Rossiyskiy Materialoveduchesky Centr, Prospect, Russian Federation

[21] Appl. No.: 244,511

[22] PCT Filed: Oct. 5, 1993

[86] PCT No.: PCT/JP93/01424

§ 371 Date: May 31, 1994

§ 102(e) Date: May 31, 1994

[87] PCT Pub. No.: WO94/17362

PCT Pub. Date: Aug. 4, 1994

[30] Foreign Application Priority Data

Jan. 19, 1993 [JP] Japan .................................... 5-023773

[51] Int. Cl.$^6$ ...................................................... G01B 9/02
[52] U.S. Cl. ........................... 356/35.5; 356/347; 356/348
[58] Field of Search ................................. 356/347, 348, 356/35.5; 359/22, 24

[56] References Cited

U.S. PATENT DOCUMENTS

| | | | |
|---|---|---|---|
| 3,911,733 | 10/1975 | Bhuta et al. | 356/35.5 |
| 3,976,380 | 8/1976 | Rottenrolber et al. | 356/348 |
| 4,702,594 | 10/1987 | Grant | 356/35.5 |

*Primary Examiner*—Samuel A. Turner
*Attorney, Agent, or Firm*—Cohen, Pontani, Lieberman, Pavane; Christa Hildebrand

[57] ABSTRACT

A new method of nondestructive testing of mechanical behaviors of objects under loading has been invented based upon the analysis of spatial and temporal distributions of velocities of deformation and rotation under elastoplastic deformation. In order to carry out this method, optical images of the surface of an object under test are obtained as holograms of a focused image, and diffraction patterns of superimposed images are then formed for a number of consecutive time points spaced with short time intervals. These diffraction patterns are then transformed into wave patterns of space and time distributions of velocities of deformation and rotation along with the respective axes. These distributions are analyzed according to the wave theory of plasticity and strength developed by the present inventors. Wave lengths, amplitudes and velocities of relaxation waves of plastic deformation are determined, and dynamics of these parameters are used to predict the time and point of eventual failure.

16 Claims, 8 Drawing Sheets

METHOD AND APPARATUS FOR NONDESTRUCTIVE TESTING OF THE MECHANICAL BEHAVIOR OF OBJECTS UNDER LOADING UTILIZING WAVE THEORY OF PLASTIC DEFORMATION

BACKGROUND OF THE INVENTION

1. Field of the Invention

The present invention is related to methods for testing materials and structures, and more specifically, to a method and apparatus for nondestructive testing of objects for their mechanical behaviors.

2. Discussion of the Prior Art

Known in the art is a method to determine stresses and strains in a loaded object, wherein the object is illuminated by coherent laser radiation before and after loading in order to obtain pairs of superimposed speckle patterns. These speckle patterns are transformed into a diffraction pattern, which is then mathematically processed. Signal amplitudes obtained by this mathematical processing are used to obtain values of strains and stresses at various points of an elastically deformed object (e.g., PCT 87/07365).

The above mentioned method is deficient because it does not allow kinetics of plastic deformation process to be analyzed since it is not designed to obtain three dimensional waves of plastic deformation. The above mentioned method permits calculation of stress and distortion fields according to the detected deformation, but does not allow one to analyze the plastic flow caused by plastic deformation. Therefore, the above mentioned conventional method is suitable only for estimation of elastic deformation and is practically unsuitable for the region of plastic deformation.

Capability to analyze the dynamics of plastic deformation is extremely important for many application problems, especially for nondestructive testing of mechanical behaviors of objects under loading since a failure is always preceded by a localized plastic deformation. Inadequacy of conventional approaches to this problem has been outstanding for a long time.

Also known are methods aimed at determining contribution of various mechanisms of plastic deformation to the actual process of plastic flow of the material and its failure (Handbook on Experimental Mechanics, Ed. by A. S. Kobayashi, Prentice-Hall 1987). All these methods are based on microscopic investigations of a defective structure of deformed material in general after the load is removed. A wide range of investigation methods are used: optical and electronic microscopy, X-ray structural analysis, various types of microscopic mechanical testing, etc.

These methods are deficient since they are highly labor intensive; they require the use of sophisticated equipment as well as requiring an extremely accurate localization of the area under examination because they employ high-resolution techniques. The critical disadvantage of these methods is the fact that they are applicable only to the analysis of residual defects of the material and not applicable to the analysis of generation and movement of defects.

The most commonly used method for obtaining data on reliability of materials (See for example Collacott R. A. "Structural Integrity Monitoring", London, Chapman and Hall 1985) consists of mechanical tests of specimens under various types of loading conditions including tension, compression, bending, torsion, crack-sample test, etc. to obtain such characteristics as elastic limit, yield limit, ultimate strength, stress intensity factor; fracture toughness, ultimate fatigue, long-time strength, etc.

These tests are generally carried out utilizing specially prepared specimens of preset shape and dimensions. Numerical values of strength and plasticity characteristics thus obtained are used for strength calculations of machine parts and structural members as well as for calculations of their reliability characteristics.

This method is deficient in that a special set of mechanical characteristics and destruction criteria is used for each type of testing. These characteristics for various types of tests are not rigorously correlated to each other, and their physical interpretations are based on numerous contradictory models which often role each other out.

Another disadvantage of this method resides in problems associated with the use of data on mechanical properties of parts of mechanisms or machines obtained under laboratory conditions rather than in actual operating conditions. A machine part in actual operation or, field-use part, is generally in a more complicated stressed state than under laboratory tests. Moreover, mechanical characteristics of the material of an actual part are influenced by the surface condition as well as by the environment. Attempts to take into account these factors during mechanical tests result in complication of the test equipment and the procedure without, however, allowing an adequate description of required data under such conditions.

Finally, the mechanical characteristics obtained during the above mentioned tests are in essence averaged over the whole volume of the specimen being tested. This makes it difficult to use these characteristics for the description of properties of polycrystalline materials with special interfaces and composites consisting of areas with varied elasticity modulus and strength properties.

A common disadvantage of all existing methods for testing of plastic materials exits in the fact that they cannot record the process itself of the development of plastic deformation, and therefore are not capable of predicting the location of future failure.

In order to solve such problems as mentioned in the above, a radically new method to analyze plastic deformation is needed which would allow dynamics of deformation to be locally studied and, in particular, prediction of behavior of objects under various actual loading conditions.

The applicant of the present patent has developed a theoretical foundation for such a new method (See for example "Structural Levels of Plastic Deformation and Failure" V. E. Panin et al., Novosibirsk, Nauka, 1990). The gist of this method of analysis of mechanical behavior of an object is based on the wave theory of plastic deformation, according to which plastic deformation and subsequent failure occur as a wave process and its parameters (i.e. wavelength, amplitude and the rate of propagation) depend on properties of the material and loading conditions. Any changes in parameters of this wave process indicates the presence of changes in the structure of the material under loading. However, when the above book was published, quantitative criteria for diagnosis of these changes were not established.

The applicant of the present patent discovered the wave nature of plastic deformation, established the theoretical basis of the phenomenon and investigated it experimentally for a simple loading condition as described in "Structural Levels of Plastic Strain and Destruction" V. E. Panin et al., Novosibirsk, Nauka, 1990.

According to the proposed scheme, the object under study is illuminated by coherent laser light and photographed. The photographic plate is exposed again after a deformation has taken place without moving the plate. After the photographic plate is chemically processed, data on plastic displacement is decoded by point scanning of the speckle photography with a narrow laser beam. Parameters of the resulting Young band diffraction pattern are measured at each point, and the modulus of a displacement vector during the period between the exposures is determined from distance between adjacent bands.

Then by spatially differentiating in respect of the axes of the coordinates, components of distortion tensor, for example, the component of shear deformation, $$\varepsilon xy = \frac{1}{2}(\Delta u/\Delta y + \Delta v/\Delta x)$$

and rotation $$\omega z = \frac{1}{2}(\Delta v/\Delta x - \Delta u/\Delta y)$$

are obtained.

Self-concordant distribution of values of plastic tensor components $\varepsilon xy$ and $\omega xy$ in an object forms a relaxation wave of plastic deformation.

The idea that wave parameters obtained in the above fashion can be used for forecasting failure of a material was suggested in the book "Structural Levels of Plastic Deformation and Failure", V. E. Panin et al., Novosibirsk, Nauka, 1990. For details see this book.

However, neither general regularities concerning the evolution of plastic deformation waves based upon increase in the degree of deformation nor the relationships between deformations and subsequent failures had been studied by that time. Quantitative criteria for forecasting failures by parameters of wave patterns under various loading conditions had not been established either. Consequently, the analysis of wave patterns could not be utilized for the development of a new method of nondestructive testing of mechanical behaviors of objects under loading.

Taking into account the above mentioned drawback of the conventional technology, the purpose of the present invention is to provide a novel and improved method and apparatus concerning the nondestructive testing of mechanical behavior of an object and the criteria to diagnose the mechanical state, by obtaining three-dimensional wave patterns of plastic deformation and variation of the plastic distortion tensor either at the testing stage or under operation.

SUMMARY OF THE INVENTION

According to an example of the method and apparatus based on the present invention, the above mentioned problem can be solved by obtaining temporally varying optical patterns of the surface of the object being tested. These optical patterns are superimposed and then converted into a diffraction pattern which contains parameters characterizing deformation taking place in the object being tested. According to the present invention, the optical pattern is obtained in the form of focused-image holograms obtained with a fixed time interval. The diffraction pattern obtained by superimposing these holographic images are converted into temporal and spatial wave patterns of the distribution of the rates of deformation and rotation having correlation with each other on an axis. By monitoring the temporal behavior of such distributions of the rate, the mechanical behavior of the object being tested can be evaluated.

In other words, the applicants of the present invention noted the wave nature of plastic deformation of an object under loading and, consequently, discovered that when a failure is about to occur, the character of the wave pattern of the material changes distinctively. The wavelength becomes commensurable with the specimen size, the wave velocity becomes equal to zero, and the wave degenerates into a one representing two localized vortices having opposite velocities. For this reason the wave pattern of plastic deformation at various stages of deformation is more informative and brings about qualitatively new criteria of plasticity, strength, reliability and destruction of material and/or structure than such conventionally used mechanical properties as yield limit, ultimate strength, work-hardening coefficient, etc. It is of critical importance that criteria of diagnosis for plasticity, strength and reliability are more universal for any plastic materials, as well as for any types and conditions of loading. Such universal criteria will allow both plastic deformation and subsequent failure to be analyzed as different phases of the same, single process. From this standpoint, the purpose of the present invention is to provide several novel and improved methods and apparatuses concerning nondestructive testing of mechanical behavior of an object and diagnostic criteria of the mechanical behavior.

From the above reason, according to the first standpoint of the present invention, it is provided a method of nondestructive testing of mechanical behavior of solid state objects under loading, said method comprising: first step for obtaining optical patterns of the object to be investigated; second step for iterating said first step with a given time interval as long as the object to be investigated is laid under external load; third step for superimposing multiple optical patterns obtained in said second step as long as the object to be investigated is laid under external load; forth step for obtaining diffraction patterns from said superimposed optical patterns obtained in said third step wherein said diffraction patterns contain parameters which characterize plastic flow of said object to be investigated; fifth step for obtaining parameters characterizing plastic flow from said diffraction patterns obtained in said forth step wherein said plastic deformation is caused by said loading of said object to be investigated; sixth step for obtaining wave patterns containing wave parameters which characterize the relaxation waves of plastic flow, which are the spatial and temporal distributions of the velocity of the deformation and rotation caused by said plastic flow of said object to be investigated, wherein the wave patterns are produced through mathematical processing of parameters obtained in said fifth step; seventh step for diagnosing the mechanical behavior of said object being laid under external load according to specific change in said wave patterns obtained in said sixth step.

In the above method, it is possible to execute the optical analysis easily by making the optical patterns obtained in said first step a hologram of a focused image of said object.

It is possible to execute the mathematical process easily by setting the interval with which said first step is iterated in said second step fixed at a value which is selected within the range which makes the deformation and rotational displacement of said object differentiable with respect to time.

It is possible to use, for example, the period of diffraction band (d) and the angle between the diffraction band and load direction (θ), wherein the diffraction band is generated by interference between light rays diffracted by the superimposed pattern, as the parameters characterizing plastic deformation contained in said diffraction patterns obtained in said forth step.

It is possible to use, for example, displacement velocity vectors of points on the surface of said object, and time derivatives of distortion tensor components such as deformation and rotation and their spatial distribution and temporal change of the distribution, as the parameters characterizing plastic flow obtained in said fifth step. It is also possible to use, for example, wavelength, amplitude, and propagation velocity of the relaxation wave of plastic flow distributing in said object, as wave parameters contained in said wave pattern.

In the seventh step, a criterion of the mechanical behavior of said object which appears as specific change in said wave pattern is characterized by whether or not the propagation velocity of said relaxation wave of plastic flow is zero, i.e., whether or not said wave is a standing wave, by whether or not the wavelength of said relaxation wave of plastic flow as a standing wave is comparable to the size of said object, or by whether or not localized vortices having the angular velocity opposite to each other are generated. The user can arbitrarily select any criterion among these criteria depending on the object being tested and/or on the testing method.

From the second standpoint of the present invention, it is provided a method for diagnosing the mechanical behavior of solid state objects under loading, said method comprising: first step for obtaining parameters characterizing plastic deformation wherein said plastic flow is caused by said loading of said object to be investigated; second step for obtaining wave patterns containing wave parameters which characterize relaxation waves of plastic flow, which are the spatial and temporal distributions of the velocity of the deformation and rotation caused by said plastic flow of said object to be investigated; third step for diagnosing the mechanical behavior of said object being laid under external load according to specific change in said wave patterns obtained in said second step.

In the method for diagnosing the mechanical behavior of a solid-state object, based on the present invention, it is also possible to use, for example, displacement velocity vectors of points on the surface of said object, and time derivatives of distortion tensor components such as deformation and rotation and their spatial distribution and temporal change of the distribution, as the parameters characterizing plastic flow. It is also possible to use, for example, wavelength, amplitude, and propagation velocity of the relaxation wave of plastic flow distributing in said object, as wave parameters contained in said wave pattern.

Similarly, a criterion of the mechanical behavior of said object which appears as specific change in said wave pattern is characterized by whether or not the propagation velocity of said relaxation wave of plastic flow is zero, i.e., whether or not said wave is a standing wave, by whether or not the wavelength of said relaxation wave of plastic flow as a standing wave is comparable to the size of said object, or by whether or not localized vortices having the angular velocity opposite to each other are generated. The user can arbitrarily select any criterion among these criteria depending on the object being tested and/or on the testing method.

In addition, according to the third standpoint of the present invention, it is provided an apparatus for nondestructive testing of the mechanical behavior of solid state objects under loading, said apparatus comprising: optical means for obtaining optical patterns of said object repetitively with a given interval for as long as said object is laid under external force; optical pattern superimposing means for superimposing multiple optical patterns obtained by said optical means; diffraction pattern forming means for obtaining diffraction patterns from said superimposed optical patterns obtained by said second optical pattern superimposing means wherein said diffraction patterns contain parameters characterizing plastic flow of said object; wave pattern forming means for obtaining wave patterns from said diffraction patterns obtained by said diffraction pattern forming means wherein said wave patterns contain wave parameters characterizing relaxation wave of plastic flow distributing in said object because of said plastic flow of said object; diagnostic means for diagnosing the mechanical behavior of said object judging from specific change in said wave patterns obtained by said wave pattern forming means.

As set forth in the above, the present invention is based on the new theoretical system established and coiltreed theoretically by the present inventors. According to this theory, plastic deformation and a resulting failure can be described by change in the field of the rate of deformation and rotational displacement of the plastic deformation. The plastic deformation wave is characterized by the process in which element phenomena of plasticity degenerate into a single wave referred to as "relaxation wave of plastic deformation" in this specification.

When the group velocity of a relaxation wave of plastic deformation decreases to be zero, the resulting standing wave degenerates into a wave representing a pair of localized vortexes of displacement. The two vortexes have angular velocities opposite to each other, and the amplitude of rotation grows continuously. Consequently, a discontinuous point is generated at the border of the two vortexes, and the discontinuity grows into a failure of the material. From this fact, a new criterion of failure, which is based on the variation of the group velocity of a relaxation wave of plastic deformation can be defined. This new criterion can be applied to the nondestructive testing method for a material/component under loading, based on the present invention.

Since the plastic deformation wave is a three dimensional wave appearing on the surface of an object under loading, it is essential to measure the wave parameter in the three dimensional space in order to apply correctly the criterion based on the fact that the group velocity of a relaxation wave of plastic deformation becomes zero. According to the present invention, measurement of wave parameters in the three dimensional space can be actualized by superimposing focused-image holograms and by processing the superimposed image.

According to an example of the present invention, the above method can be actualized by a nondestructive testing apparatus comprising a optical means for obtaining optical patterns of the surface of the object being examined; a diffraction pattern forming means for obtaining diffraction patterns from the obtained optical patterns of the surface and a mathematical means for processing parameters of the obtained pattern. In the present invention, the means for obtaining optical patterns is designed to obtain focused-image holograms and a unit capable of calculating temporal and spatial distribution of deformation and rotation using parameters of the diffraction pattern is provided in the mathematical means. For the purpose of obtaining wave patterns, the output of the present apparatus is connected to a visualization apparatus.

DESCRIPTION OF THE REFERRED EMBODIMENTS

Figure 1:
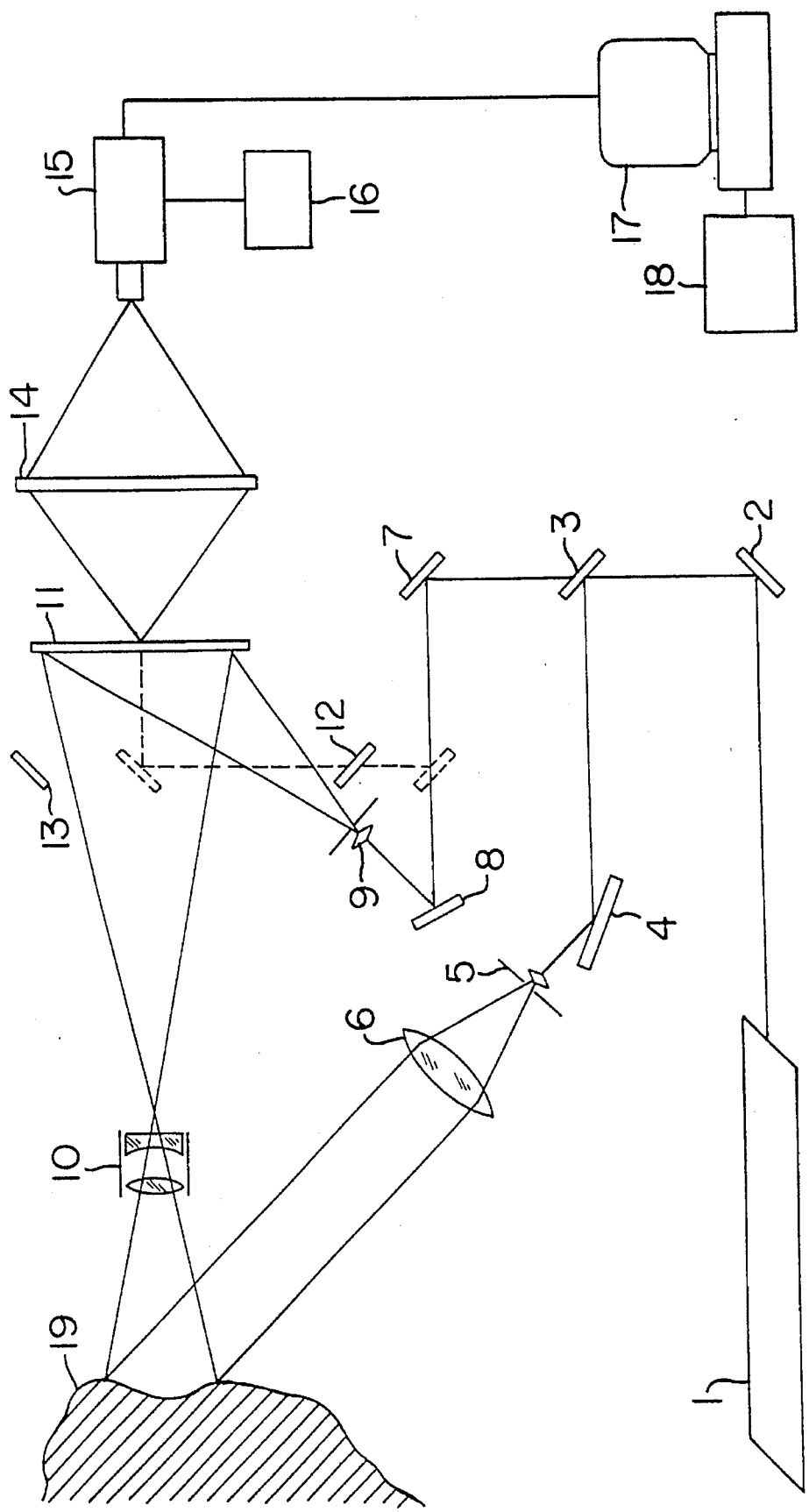
FIG. 1 is a schematic illustration of an apparatus for nondestructive testing of the mechanical behavior of an object with the use of the wave theory of plastic deformation.

The preferred embodiment of the present invention will now be described below in connection with the accompanying drawings, however, it is understood that the present invention is not limited to the under-described embodiments.

Before the method of nondestructive testing of the mechanical behavior of an object under the present invention is discussed, reference is made to an embodiment of the apparatus. The gist of the method will become clear from the description of the operation of the apparatus.

The example apparatus for nondestructive testing has a laser 1 of any known type, e.g., a He-Ne laser with an output chosen so as to provide an exposure of maximum 1 second to record a hologram.

The optical system of the apparatus has two optical channels one of which is designed for forming a collimated object beam and has a reflecting mirror 2, a semitransparent mirror 3, a reflecting mirror 4, a beam expander 5, and a collimating lens 6. The other channel is designed for producing a reference beam and has mirrors 2 and 3, mirrors 7 and 8, and a beam expander 9. Moreover, the optical system has an objective 10 for constructing an object image on a carrier 11, e.g., on a photographic plate, mounted on a holder (not shown). The holder is movable in two mutually perpendicular directions for the purposes to be described below. It will be apparent that after an exposure a hologram of focused image can be obtained on the carrier.

The system also has an optical decoder formed by mirror 12 and 13 to produce a beam of 0.8 mm in diameter for exposing the hologram and obtaining a diffraction pattern on a screen 14. Mathematical processing of a hologram formed on carrier 11 is accomplished by means of a computing unit which has a system 15 for inputting analog signals and converting them to digital signals.

The analogue/digital convening system 15 may be in the form of a digital output video camera. The output of system 15 is connected to a display 16 and a computer 17. The computer software is compiled in such a way as to obtain values of deformation rates and rates of rotation which are determined from the diffraction pattern on screen 14 and are shown as distributions of these values along chosen or preset directions. A wave pattern of plastic deformation is thus produced at the computer output. Observing the dynamics of this pattern allows deformation of an object to be estimated.

This wave pattern can be reproduced by means of a plotter 18.

The apparatus functions in the following manner. Radiation of laser 1 is split by the mirror system into two beams. One beam is the object beam and is fed to the collimator to illuminate an object 19 with a planar wave of light. The second beam is used as a reference beam and is directed to photographic plate 11. The intensity ratio of the two beams is chosen empirically by means of a semitransparent mirror 3 which functions as a beam splitter.

Objective 10 constructs an image of object 19, which is illuminated with coherent light, in the plane of photographic plate 11. A first exposure on the photographic plate is carried out. The exposure time is chosen empirically. Object 19 is then deformed for a short preset time $\Delta t$. (Deformation may be caused by a load application, variation of temperature or environment conditions, etc.) After the lapse of a preset time, e.g., 40–80 sec, a double exposure of the same photographic plate is carried out. Two superimposed holograms of a focused image, which also have properties of the specklephotographs, are thus recorded on the photographic material.

The whole process is then repeated with a new interval or with the same small interval $\Delta t$. The resulting series of double exposure holograms of the focused image allow the entire process of deformation which has taken place during the study period to be recorded. In an embodiment in which a video camera is used for hologram recording, a direct recording and processing of obtained images by a digital computer will be made.

Data on values of vectors of displacement velocities at all points of the object surface is thus recorded in a superimposed holographic image. This data can be reproduced by means of an optical processing of the resulting image. In case the image is recorded on a photographic plate, the latent photographic image is first transformed by developing and fixating into a visible negative image. The hologram is then placed into the holder and is illuminated with the same reference beam as was used during the recording. The object image with superimposed lines of equal displacements along an axis drawn perpendicularly with respect to the surface is inputted in computer 17 by means of system 15 for processing and computing components of displacement velocities $\dot{w}$ (along axis z). The observed pattern is monitored on display 16.

The displacement velocities in the plane of the object surface (along axes x and y) are determined by processing a speckle-structure of the object image. For this purpose line-by-line scanning of the superimposed image at 1 mm step is performed with a narrow beam formed by mirrors 12, with a Young bands diffraction pattern produced at each point. This pattern is recorded by system 15, digitized, and put into the computer in which the band spacing d and angle $\theta$ of band inclination with respect to axis x are determined.

The following formula is then used to find the value of displacement velocity vector in plane x-y:

$$\tilde{r} = 1/\Delta t * \lambda s/d$$

and then the following formula are used to find the components of a tensor of velocity of plastic deformation of the object.

$\dot{u} = \tilde{r} \cos\theta,$
$\dot{v} = \tilde{r} \sin\theta,$
$\dot{\varepsilon}_{xx} = \partial\dot{u}/\partial x,$
$\dot{\varepsilon}_{yy} = \partial\dot{v}/\partial y,$ $\dot{\varepsilon}xy=\frac{1}{2}\{\delta\dot{u}/\delta y+\delta\dot{v}/\delta x\}$,
$\dot{\omega}z=\frac{1}{2}\{\delta\dot{v}/\delta x-\delta\dot{u}/\delta y\}$, $\dot{\varepsilon}xx$, $\dot{\varepsilon}yy$, $\dot{\varepsilon}xy$, and $\dot{\omega}z$ obtained by the above equations are evaluated consecutively along a chosen axis (e.g., the tension axis) and plotted by a plotter. Then from the dynamics of their changes the behavior of the material under loading in the object being tested will be estimated. Analysis of the behavior of the material before failure is based on the new theoretical and experimental wave criteria of strength and failure established by the inventors.

Figure 2:
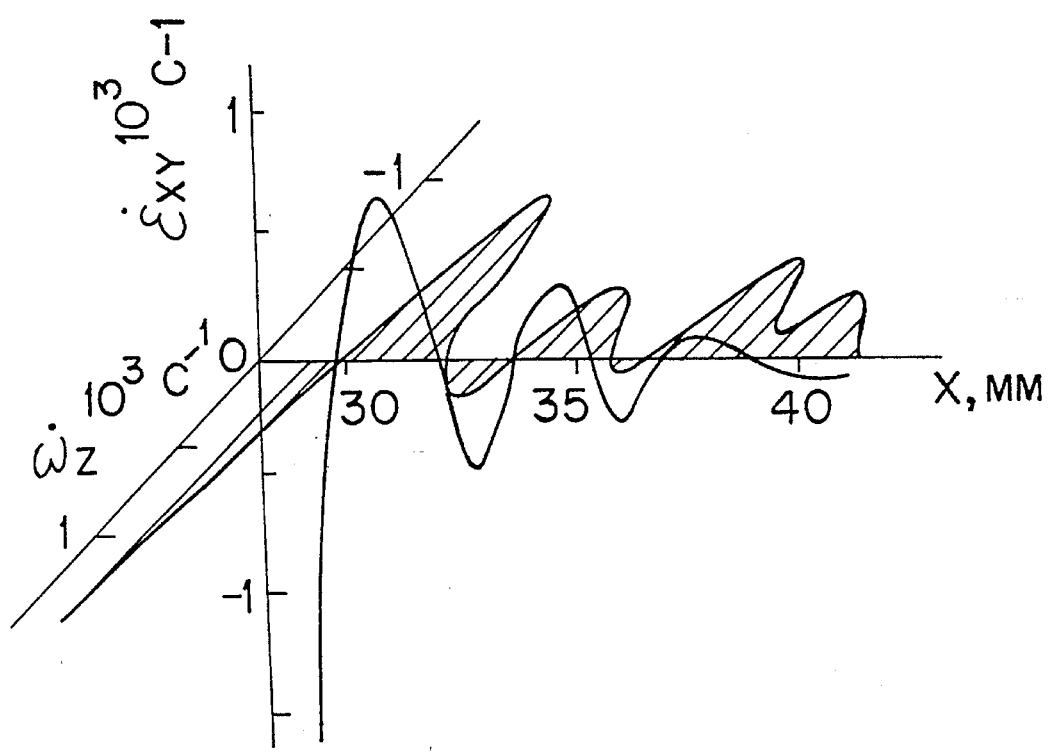
FIG. 2 shows a relaxation wave of plastic deformation in Fe+3%Si obtained by means of the apparatus shown in FIG. 1.
Figure 3:
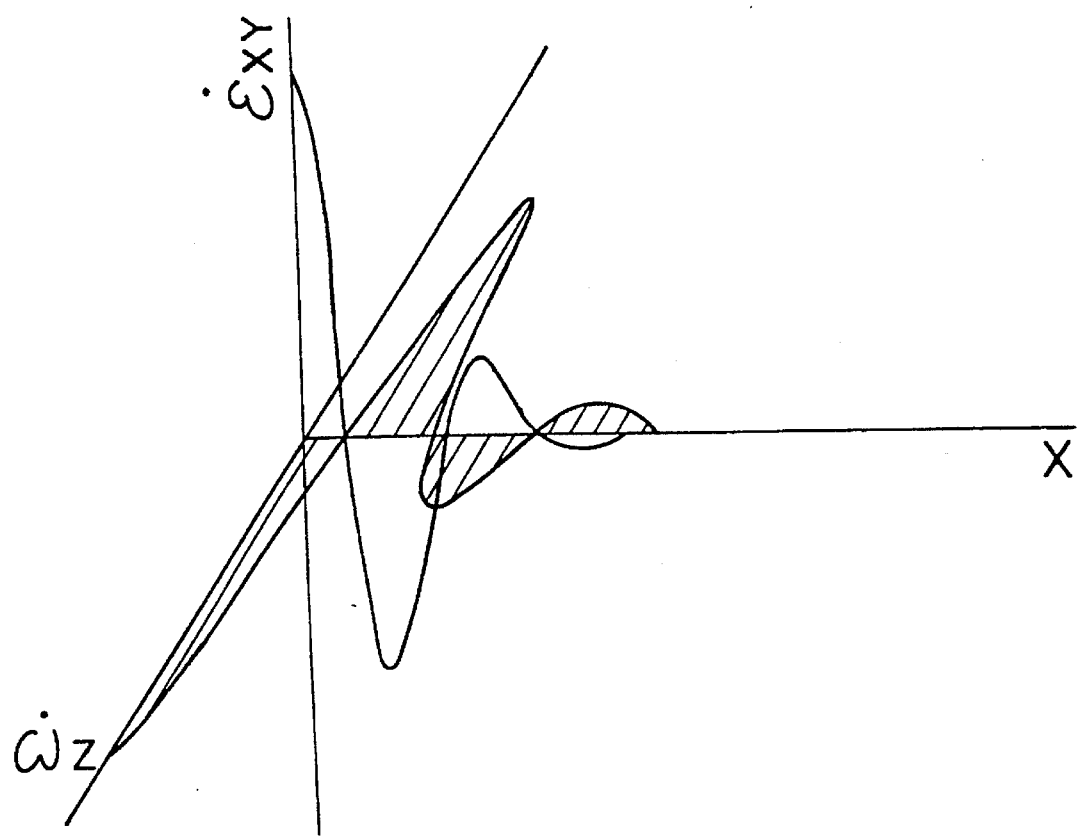
FIG. 3 shows a relaxation wave of plastic deformation obtained by a theoretical technique with the use of a wave model of plastic deformation.

An example of such a relaxation wave of plasticity for tensile strain of a specimen of Fe+3%Si alloy obtained in this manner is shown in FIG. 2. For comparison, results of a theoretical calculation of a wave pattern for a similar case is shown in FIG. 3. A fair agreement between the experimental and theoretical results adds to confirmation of validity of the wave theory of plastic deformation and its usefulness as a basis for finding out criteria of strength and failure in terms of wave parameters.

For a better understanding of the essence of the present invention, concrete examples will be described with reference to specific test specimens.

Example 1

Monitoring of tensile plastic deformation in a steel specimen will be described. Image forming and its processing were carried out as described above.

The working part of the specimen was sized 3×10×60 mm. The specimen was tensioned on "Instron" testing machine at a rate of $2\times10^{-5}$ s$^{-1}$. Indicator deformation diagram was recorded during testing. The entire tension process was divided into stages at a step of 0.2% as follows: 0–0.2–0.4–0.6–0.8–1.0–1.2–1.4–1.6–1.8 –2.0–2.2%–... of total deformation each point.

Let us discuss the stage of 0.4–0.6% deformation. When the total elongation of the specimen reached 0.4%, the apparatus of FIG. 1 was used to record the focused image hologram on a photographic plate. 100 seconds thereafter when deformation reached 0.6%, a second hologram was recorded on the same photographic plate without moving the plate. Two superimposed images (double-exposure hologram) were thus produced. This hologram was then subjected to a conventional chemical treatment including development and fixating of the recorded double image. As a result, a photographic plate (negative) with a specimen image at a 1:1 scale was obtained on which all data of deformation distribution in the specimen at this stage of tension were recorded.

The next stage is a decoding of the obtained data. For this purpose, the resulting double-exposure hologram was scanned with a narrow laser beam (0.8 mm in diameter) formed by mirrors 12, 13 at all individual points with 1 mm steps to embrace the entire field of the specimen image. The scanning was performed by means of a hologram holder (see above) with built-in step motors. At each exposure to laser light, diffraction bands spaced at d and inclined at an angle $\theta$ with respect to the tension axis were formed. These values were put into computer 17 by system 15 and were automatically measured, and velocities of displacement of individual points (time-derivative) were then calculated as follows:

$$\dot{r}=1/\Delta t * \lambda s/d$$

where $\lambda=0.63\times10^{-6}$ m is the laser wavelength, d is the distance between the diffraction bands (meter), S is the distance from the hologram to the screen (meter), $\Delta t=10^2$ is the time interval between the two exposures at 0.4 and 0.6% of the total deformation.

Furthermore, time derivatives of shear deformation and rotation were calculated by computer 17. Axis x was chosen to be aligned with the tension axis, and axis y was drawn in the plane of the observed surface (x and y are perpendicular to each other). The calculations were carried out as follows:

$\dot{\varepsilon}xy=\frac{1}{2}\{\delta\dot{u}/\delta y+\delta\dot{v}/\delta x\}$,
$\dot{\omega}z=\frac{1}{2}\{\delta\dot{v}/\delta x-\delta\dot{u}/\delta y\}$, where $\dot{u}=\dot{r}\cos\theta$, $\dot{v}=\dot{r}\sin\theta$.

Figure 4:
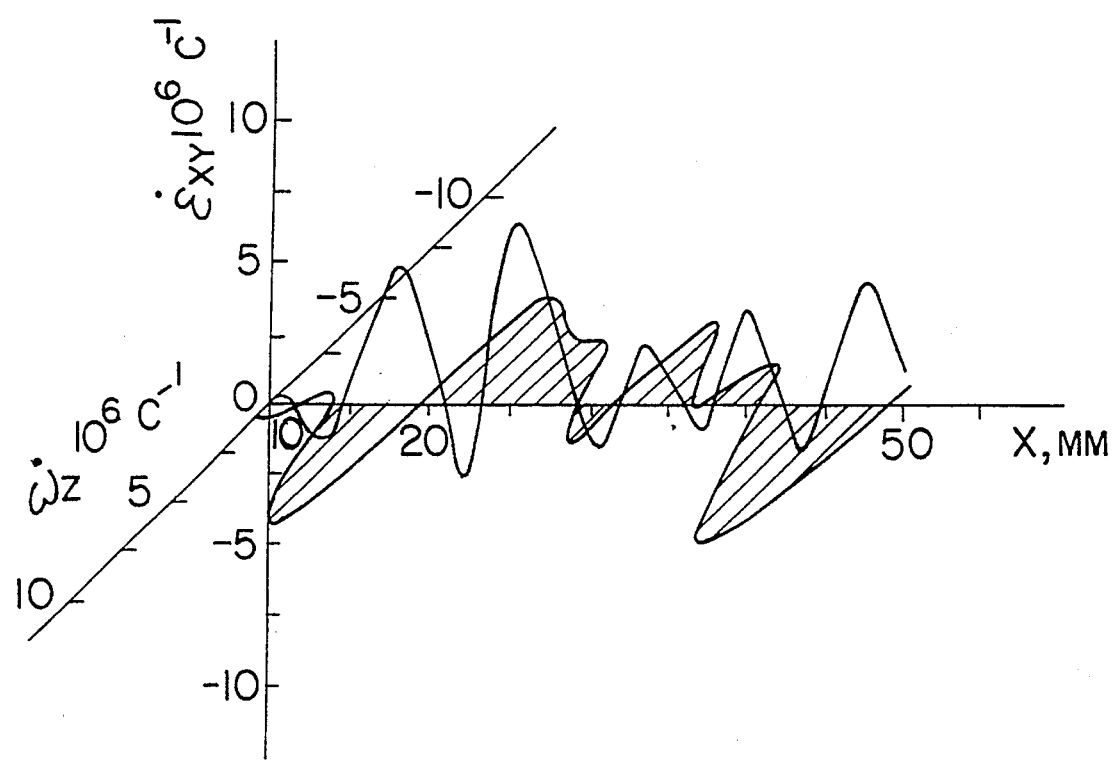
FIG. 4 shows a relaxation wave of plastic deformation in steel obtained by means of the apparatus shown in FIG. 1.

Mathematical processing of the values of $\dot{\varepsilon}xy$ and $\dot{\omega}z$ allowed relaxation waves of plastic deformation to be experimentally observed on a display or plotter (FIG. 4). When the measuring and processing procedures described above were repeated for stages 0.6–0.8, 0.8–1.0, 1.0–1.2%, similar distribution patterns of $\dot{\varepsilon}xy$ and $\dot{\omega}z$ along the tension axis were obtained. The offsets of one of the peaks of $\dot{\varepsilon}xy$ and $\dot{\omega}z$ along the axis were used respectively to determine the respective velocity of propagation of the relaxation wave of plastic deformation: $10^{-5}$ m/s, $$Vrv=\Delta l/\Delta t\cong 10^{-5} \text{ m/s}$$

where $\Delta l$ is the offset of the peak in the time period $\Delta t$ ($l=10^{-3}$ m). Thus, the plastic waves propagating throughout the object at this stage of deformation can be obtained.

An absolutely different distribution pattern of $\dot{\varepsilon}xy$ was obtained by the same procedure beginning with stage 1.6–1.8%. When all the steps described above were repeated, a pattern shown in FIG. 5 was obtained.

Figure 5A:
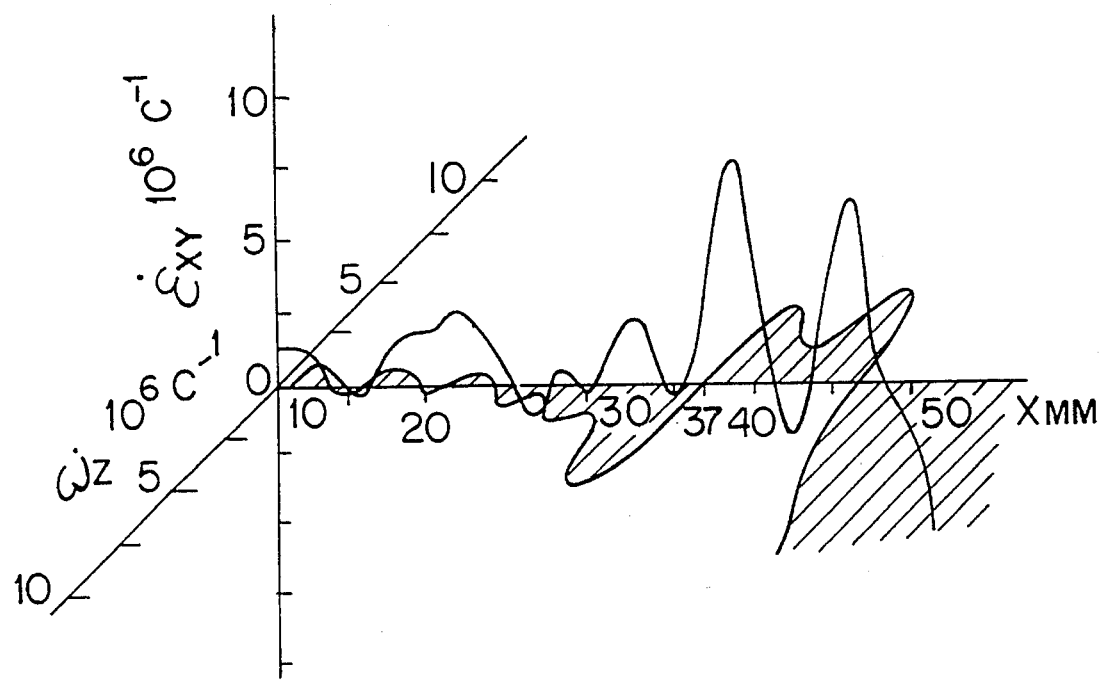
FIG. 5 shows a relaxation wave of plastic deformation of the same specimen as that shown in FIG. 4 at the moment of origination of failure, the photograph showing the failed specimen.
Figure 5B:
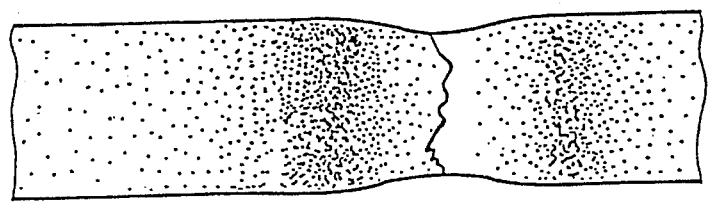

Two characteristic regions exist in FIG. 5: at 0<x<37 mm the respective velocities of shear deformation and rotation were close to zero ($\dot{\varepsilon}xy\cong 0$, $\dot{\omega}z\cong 0$). In the region x>37 mm, amplitudes of these velocity waves were high and continued to increase. Upon further measurements propagation of the relaxation wave of plastic deformation along the tension axis x came to a complete stop (Vrv=0). The above is indicative of a strong concentration of deformation and origination of failure at point x=37 min. As shown by further investigations, when the loading was continued at the same rate of $2\times10^{-5}$ s, the specimen failed at point x=37 mm at the moment the total deformation reached the value of 2.67% (FIG. 5).

In this way, a change in the plasticity wave pattern gives an indication of origination of failure. Interruption of the relaxation wave propagation process and formation of a standing wave with a wavelength commensurable with the object size are the criteria of origination of failure.

Example 2

To prove the applicability of the present method of nondestructive testing for the purpose of analyzing of material conditions in a weld area, plastic deformation patterns were analyzed with regard to in an area known to include a welded zone. A specimen with a size of 20×30×120 mm made of two steel strips connected by electric welding was used. The weld was not revealed in advance, and it was not possible to locate the weld on the specimen with naked eyes. The specimen was tensioned at a rate of $10^{-5}$ s$^{-1}$. At a deformation of 0.6% a first photograph was taken with recording of a hologram of focused image 11. Then, after a lapse of $\Delta t=1$ min, at a total deformation of 0.66%, a second hologram was recorded on the same photographic plate. They were visualized by means of conventional chemical treatment of the photographic material after the exposure (development and fixation).

Figure 6A:
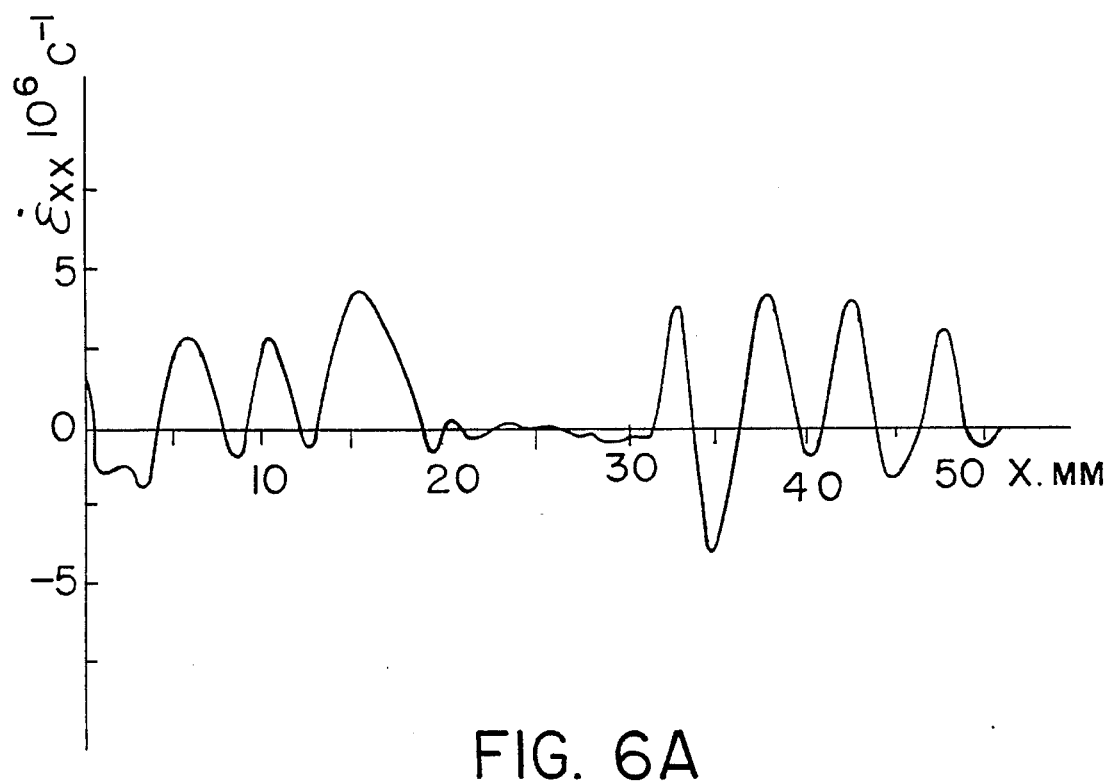
FIG. 6 shows a relaxation wave of plastic deformation of a specimen having a weld; the weld zone is revealed by metallography.
Figure 6B:
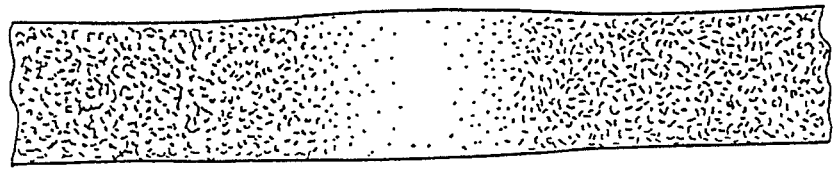

Decoding of the recorded data on displacements of points on the object surface under plastic deformation was accomplished by the optical processing technique as described above by transforming an optical image to a diffraction pattern. This was achieved through a line-by-line scanning of the superimposed image with a narrow laser beam of 0.8 mm in diameter. The resulting diffraction pattern consisting of Young bands was put into computer 17 by system 15 to determine band spacing d and their angle of inclination θ with respect to the tension axis as described above. The displacement velocity vector in the object surface plane was then calculated as follows:

$$\bar{r} = 1/\Delta t * \lambda s/d$$

where $\lambda = 0.63 \times 10^{-6}$ m is the laser radiation wavelength, s is the distance from the hologram to the screen during decoding. The velocity of tensile plastic deformation $\dot{\varepsilon}xx$ was used as an informative parameter, which was determined by computer 17 as follows:

$\dot{\varepsilon}xx = \delta\dot{u}/\delta x$, where $\dot{u} = \bar{r} \cos\theta$. The obtained data are shown in FIG. 6 in the form of $\dot{\varepsilon}xx$ so that the point of eventual failure may be predicted.

It is well known that welded joints always fail across a thermal influence zone. In FIG. 6 this zone is characterized by points with coordinates x=20 mm and x=32 mm. Rates of plastic deformations in the weld zone 20<x<30 mm are low, but they suddenly rise in the thermal influence zones, i.e., the relaxation wave of plastic deformation does not propagate into the weld area, and the deformation concentrates in thermal influence zones. With further loading, failure occurred in a section at x=32 mm across the thermal influence zone. Therefore, this example attests to the fact that the point of failure of a welded structure can be predicted with the use of criterion that the group velocity of relaxation wave of plastic deformation becomes zero.

Example 3

Figure 7A:
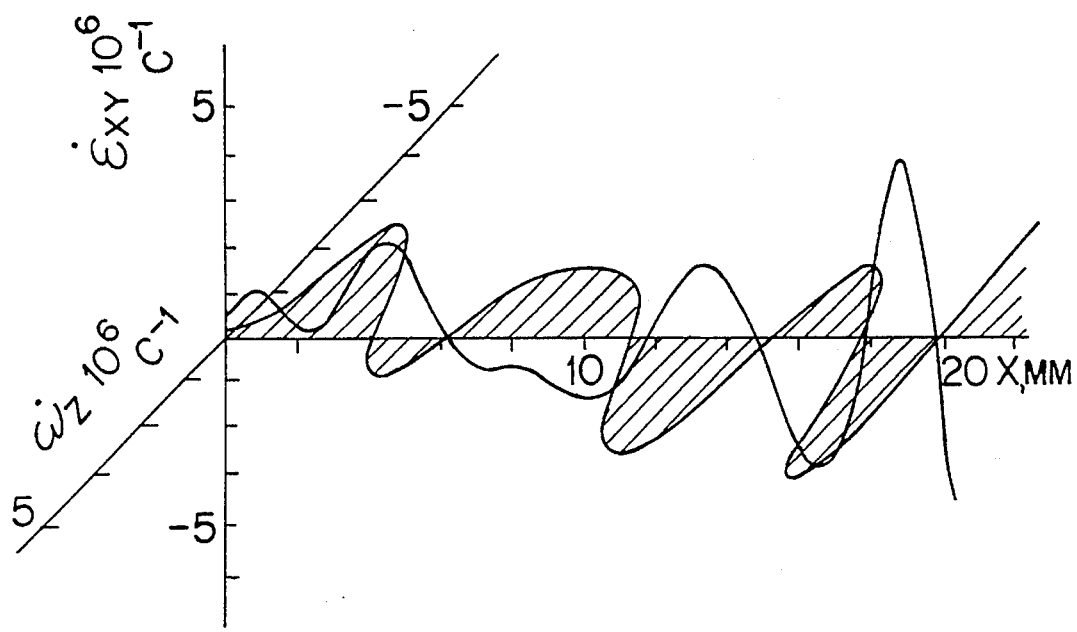
FIG. 7 shows a relaxation wave of plastic deformation in an aluminium specimen and a calculated pattern of vortices of deformation velocities in a failure origination zone.
Figure 7B:
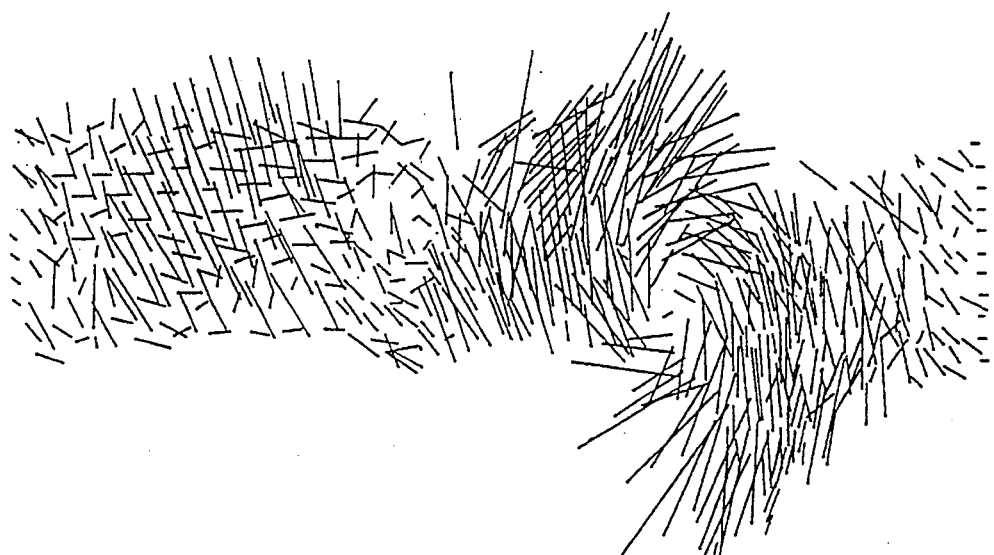

Plastic deformation of pure aluminium was investigated. A specimen of 8×70×1.5 mm in size was tensioned on "Instron" testing machine at a rate of $5 \times 10^{-5}$ s$^{-1}$. A grain size was 10–15 mm so that the specimen had only 6 crystals. At the stage of 0.5–0.6% deformation, a wave pattern shown in FIG. 7 was obtained by means of the apparatus described above and by using the above described procedure. The resulting data were then extrapolated with the help of the wave theory to the region of large strains (5%), and a displacement velocity field was constructed (FIG. 7). It turned out that at this stage of deformation two opposite vortices were formed in the material which can be clearly seen in FIG. 7. The boundary between two vortices, which corresponds to the area of x=20 mm, indicates the point of origination of failure. Upon further tension a neck was formed in this area, and then, at a total deformation of 30% the specimen failed viscously in this zone. The wave pattern proved suitable for predicting the place of failure.

Example 4

Figure 8:
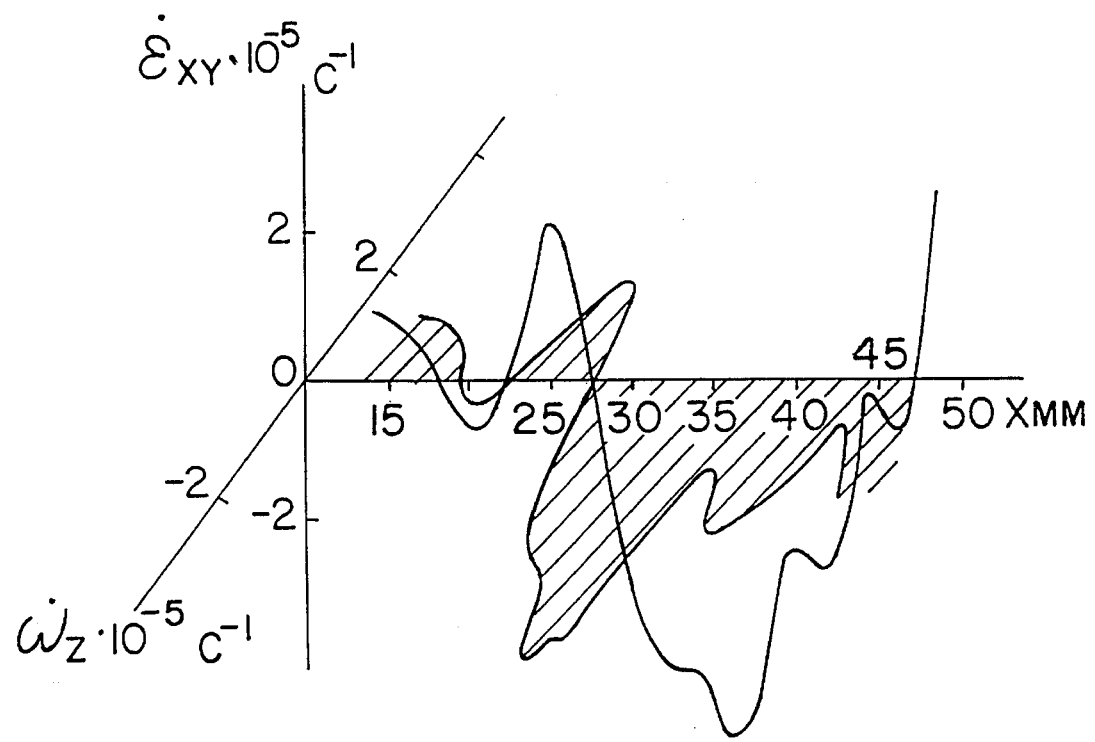
FIG. 8 shows a relaxation wave of plastic deformation in an amorphous material.

Deformation of amorphous alloy $Fe_{40}Ni_{40}B_{20}$ was studied. Specimens in the form of a strip 50 mm long, 15 mm wide and 22 mm thick were tensioned at a rate of 10 s$^{-1}$ on "Instron" testing machine. The procedure of tests and result handling did not differ from the above examples. However, total deformations in this case were small and ranged between 0.1 and 0.2%. Distribution of velocities of shear deformation and rotation in the specimen shown in FIG. 8 shows that a relaxation wave of plastic deformation is formed in the amorphous material even at this stage, and the characteristic distribution of shear deformation and rotation should cause a failure if the active loading is continued. This is due to the fact that two areas at x<27 mm and x >27 mm have been revealed in which the shear deformation and rotation velocities were different in amplitude and direction, i.e., two non-compensation vortices develop in this area. The boundary between them at x=27 mm is a potential point of failure. During a further application of the same tension on the specimen it did fail in the section at x =27 mm. This confirms the fitness of the prediction criterion used for forecasting the point of eventual failure.

Industrial Applicability

As described above, The present invention allows one to obtain a relaxation wave of plastic deformation which appears as a three-dimensional wave on the surface of the object under loading, by superimposing focused image holograms and processing the superimposed image. By applying the criteria of failure based on the fact that the group velocity of the relaxation wave, one can describe plastic deformation of the object being tested and predict potential failure resulting from the plastic deformation. Thus the present invention is suitable for nondestructive testing and diagnosing the mechanical state of a solid-state object.

This method under the present invention can be used for estimating stressed or strained states of machines, structures, and devices all of which are loaded under the real world operating conditions such as high-pressure vessels, pipelines, load-bearing structures, power plant equipment, chemical reactors, steam boilers, turbines and engine casings, etc. This method is also promising for investigations of plastic deformation and mechanisms of failure in research and for determining strength and reliability characteristics of new materials as well as for testing of objects under conditions close to actual operating conditions.

What is claimed is:
1. A method of nondestructive testing of the mechanical behavior of solid state objects under loading, said method comprising:
   first step for obtaining optical patterns of the object to be investigated;
   second step for iterating said first step with a given time interval as long as the object to be investigated is laid under external load;
   third step for superimposing multiple optical patterns obtained in said second step as long as the object to be investigated is laid under external load;
   forth step for obtaining diffraction patterns from said superimposed optical patterns obtained in said third step wherein said diffraction patterns contain parameters which characterize plastic flow of said object to be investigated;
   fifth step for obtaining parameters characterizing plastic flow from said diffraction patterns obtained in said forth step wherein said plastic flow is caused by said loading of said object to be investigated;
   sixth step for obtaining wave patterns containing wave parameters which characterize relaxation waves of plastic flow, which are the spatial and temporal distributions of the velocity of the deformation and rotation caused by said plastic flow of said object to be investigated, wherein the wave patterns are produced through mathematical processing of parameters obtained in said fifth step;

seventh step for diagnosing the mechanical behavior of said object being laid under external load according to specific change in said wave patterns obtained in said sixth step.

2. A method of nondestructive testing of the mechanical behavior of solid state objects under loading as claimed in claim 1, wherein the optical patterns obtained in said first step are holograms of a focused image of said object.

3. A method of nondestructive testing of the mechanical behavior of solid state objects under loading as claimed in claim 1, wherein the interval with which said first step is iterated in said second step is fixed at a value which is selected within the range which makes the deformation and rotational displacement of said object differentiable with respect to time.

4. A method of nondestructive testing of the mechanical behavior of solid state objects under loading as claimed in claim 1, wherein the parameters characterizing plastic flow contained in said diffraction patterns obtained in said forth step are the period of diffraction band (d) and the angle between the diffraction band and load direction (θ), wherein the diffraction band is generated by interference between light rays diffracted by the superimposed pattern.

5. A method of nondestructive testing of the mechanical behavior of solid state objects under loading as claimed in claim 1, wherein the parameters characterizing plastic flow obtained in said fifth step are displacement velocity vectors of points on the surface of said object, and time derivatives of distortion tensor components such as deformation and rotation and their spatial distribution and temporal change of the distribution.

6. A method of nondestructive testing of the mechanical behavior of solid state objects under loading as claimed in claim 1, wherein said wave parameters contained in said wave pattern obtained in said fifth step are wavelength, amplitude, and propagation velocity of the relaxation wave of plastic flow distributing in said object.

7. A method of nondestructive testing of the mechanical behavior of solid state objects under loading as claimed in claim 1, wherein a criterion of the mechanical behavior of said object which appear as specific change in said wave pattern in said seventh step is characterized by whether or not the propagation velocity of said relaxation wave of plastic flow is zero, i.e., whether or not said wave is a standing wave.

8. A method of nondestructive testing of the mechanical behavior of solid state objects under loading as claimed in claim 1, wherein a criterion of the mechanical behavior of said object which appear as specific change in said wave pattern in said seventh step is characterized by whether or not the wavelength of said relaxation wave of plastic flow as a standing wave is comparable to the size of said object.

9. A method of nondestructive testing of the mechanical behavior of solid state objects under loading as claimed in claim 1, wherein a criterion of the mechanical behavior of said object which appear as specific change in said wave pattern in said seventh step is characterized by whether or not localized vortices having the angular velocity opposite to each other are generated.

10. A method for diagnosing the mechanical behavior of solid state objects under loading, said method comprising:

first step for obtaining parameters characterizing plastic flow wherein said plastic flow is caused by said loading of said object to be investigated by optical means;

second step for transforming parameters obtained in said first step by processor means to wave patterns containing wave parameters which characterize relaxation waves of plastic flow, which are the spatial and temporal distributions of the velocity of the deformation and rotation caused by said plastic flow of said object to be investigated;

third step for observing the wave patterns obtained in said second step to diagnose the mechanical behavior of said object being laid under external load according to specific change.

11. A method for diagnosing of the mechanical behavior of solid state objects under loading as claimed in claim 10, wherein the parameters characterizing plastic flow obtained in said first step are displacement velocity vectors of points on the surface of said object, and time derivatives of distortion tensor components such as deformation and rotation and their spatial distribution and temporal change of the distribution.

12. A method for diagnosing of the mechanical behavior of solid state objects under loading as claimed in claim 10, wherein said wave parameters contained in said wave pattern obtained in said second step are wavelength, amplitude, and propagation velocity of the relaxation wave of plastic flow distributing in said object.

13. A method for diagnosing of the mechanical behavior of solid state objects under loading as claimed in claim 10, wherein a criterion of the mechanical behavior of said object which appear as specific change in said wave pattern in said third step is characterized by whether or not the propagation velocity of said relaxation wave of plastic flow is zero, i.e., whether or not said wave is a standing wave.

14. A method for diagnosing of the mechanical behavior of solid state objects under loading as claimed in claim 10, wherein a criterion of the mechanical behavior of said object which appear as specific change in said wave pattern in said third step is characterized by whether or not the wavelength of said relaxation wave of plastic flow as a standing wave is comparable to the size of said object.

15. A method for diagnosing of the mechanical behavior of solid state objects under loading as claimed in claim 10, wherein a criterion of the mechanical behavior of said object which appear as specific change in said wave pattern in said third step is characterized by whether or not localized vortices having the angular velocity opposite to each other are generated.

16. An apparatus for nondestructive testing of the mechanical behavior of solid state objects under loading, said apparatus comprising:

an optical means for obtaining optical patterns of said object repetitively with a given interval for at long as said object is laid under external force, an optical means for superimposing multiple optical patterns obtained by said optical means, for obtaining optical patterns, a diffraction pattern forming means for obtaining diffraction patterns from said superimposed optical patterns obtained by said second optical pattern superimposing means wherein said diffraction patterns contain parameters characterizing plastic flow of said object, a wave pattern forming means for obtaining wave patterns from said diffraction patterns obtained by said diffraction pattern forming means wherein said wave patterns contain wave parameters characterizing relaxation wave of plastic flow distributing in said object because of said plastic flow of said object, a diagnostic means for diagnosing the mechanical behavior of said object judging from specific change in said wave patterns obtained by said wave pattern forming means.

* * * * *